United States Patent

Dare et al.

Patent Number: 5,591,154
Date of Patent: Jan. 7, 1997

[54] DISPOSABLE ABSORBENT PRODUCT

[75] Inventors: Karen Dare, Binfield Bracknell Berkshire; Martin Riswick, Marlow, both of United Kingdom; Gary F. Raykovitz, Flemington; Charles W. Paul, Madison, both of N.J.

[73] Assignee: National Starch and Chemical Investment Holding Corporation, Wilmington, Del.

[21] Appl. No.: 449,502

[22] Filed: May 24, 1995

[51] Int. Cl.$^6$ ........................................... A61F 13/15
[52] U.S. Cl. ........................................... 604/387; 604/367
[58] Field of Search ........................... 604/386–392, 604/372, 367

[56] References Cited

U.S. PATENT DOCUMENTS 4,136,699  1/1979  Collins et al. .................. 128/290 R
4,704,110  11/1987  Raykovitz et al. .................. 604/366

OTHER PUBLICATIONS

Firestone Synthetic Rubber & Latex Company, Akron, OH, "Stereon®", Technical Literture.

"New Modified TPE Polymers", David J. Dougherty, Firestone Synthetic Rubber & Latex Company, 1994 Hot Melt Symposium, pp. 115–123.

*Primary Examiner*—Robert A. H. Clarke
*Attorney, Agent, or Firm*—Karen G. Kaiser; Ellen T. Dec

[57] ABSTRACT

This invention discloses that styrene-butadiene-styrene block copolymers containing 30 to 50% by weight styrene and additionally having been polymerized in such a manner as to obtain a vinyl content of greater than about 35% may be used in adhesives to achieve desirable low viscosity of 1000 to 3500 cps at 160° C.

12 Claims, 1 Drawing Sheet

DISPOSABLE ABSORBENT PRODUCT

BACKGROUND OF THE INVENTION

A variety of absorbent structures, for example, sanitary napkins, panty liners and the like, are constructed using pressure sensitive adhesives as positioning adhesives for attaching the article to the supporting garment.

There are a number of critical properties needed for these applications, specifically, the viscosity profile must be such that the adhesive will flow onto and partially penetrate the surface to which it is applied, yet allow a significant amount of the adhesive to remain on the exposed surface. Further, the adhesive coating must have good bond strength with high initial tack, yet the adhesive film must not transfer to the garment or cause pulling of the fibers or tearing of the garment when the absorbent article is removed.

Hot melt pressure sensitive adhesives are most commonly used for this positioning purpose with those disclosed in U.S. Pat. Nos. 4,136,699 and 4,704,110, being representative of the adhesives in current commercial use.

It has been proposed in U.S. Pat. No. 4,704,110 to utilize high styrene containing polymers, i.e., those containing greater than 35% styrene, in order to provide adhesives for positioning sanitary products to undergarments.

The commercial polymers referred to in the '110 patent generally had styrene contents in the range of 35 to 55 parts per 100 parts copolymer. Moreover, the block copolymers contained relatively low levels, i.e., less than about 15%, of divinyl functionality as a consequence of the actual polymerization reaction.

While the adhesives formulated therewith exhibited superior properties as contrasted with those available commercially at the time; there is a continuing need for adhesives exhibiting lower viscosity at temperatures of 130° to 160° C. which will enable the product to penetrate readily through the non-woven, thus allowing the positioning adhesive to also function as a construction adhesive.

SUMMARY OF THE INVENTION

We have now found that the use of styrene-butadiene-styrene block copolymers containing 30 to 50%, preferably 40 to 50%, by weight styrene and additionally having been polymerized in such a manner as to obtain a vinyl content of greater than about 35%, preferably 42 to 46%, may be used in adhesives to achieve desirable low viscosity of 1000 to 3500 cps at 160° C. Moreover, the adhesives are characterized by high heat resistance, superior tensile strength, high softening point, and moderate peel, further exhibiting no transfer to the undergarments. As such, these block polymers are ideally suited for use in positioning adhesive formulations.

Thus, the present invention is directed to an absorbent product comprising an elongated absorbent pad having a body facing surface and a garment facing surface, a portion of the garment facing surface being coated with the hot melt adhesive composition comprising:

15 to 40% by weight of a styrene-butadiene-styrene block containing 30 to 50% styrene, the block copolymer having been polymerized so as to have a vinyl content greater than 35%

30 to 70% by weight of a tackifying resin selected from the group consisting of C5–C10 aliphatic or cycloaliphatic petroleum hydrocarbon resins having a Ball and Ring softening point of 70° to 150° C.; modified hydrogenated rosins; glycerol and pentaerythritol esters of modified hydrogenated rosins; copolymers and terpolymers of natural terpenes; polyterpene resins having a softening point, as determined by ASTM method E28-58T, of from about 80 to 150° C.; aromatic petroleum hydrocarbon resins and the hydrogenated derivatives thereof; and copolymers of aliphatic and aromatic monomers;

10 to 30% by weight of naphthenic or paraffinic oil; and 0.1 to 2% by weight of an antioxidant; characterized in that the viscosity of the adhesive is 1000 to 3500 cps at 160° C.

In a preferred embodiment of the invention, the hot melt adhesive is applied to the pad in a manner such that it serves as both a positioning and construction adhesive.

DETAILED DESCRIPTION OF THE PREFERRED EMBODIMENTS

Figure 1:
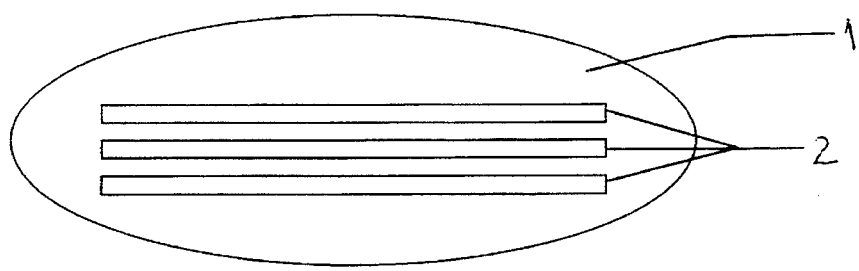
FIG. 1 depicts a top view of a representative absorbent product.

While the incorporation of relatively high levels of styrene in block copolymers has been known for some time, it is only recently that the high styrene containing block copolymers have been polymerized in such a manner as to produce a high vinyl content in the mid-block portion. Thus, block copolymers previously used in disposable applications have been characterized by a mid-block polymeric structure which is primarily of the following trans-1,4-butadienyl or cis-1,4-butadienyl configurations:

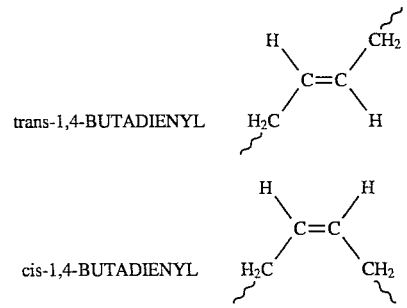

In contrast, the polymers used herein contain substantial amounts, i.e., greater than about 35% of the copolymer, of the vinyl modified butadiene, i.e., in the form of the 1,2-butadienyl composition as represented by the formula:

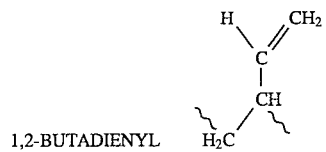

Various modifiers can produce butadiene polymerization changes from primarily a cis-trans structure to one containing high levels of vinyl structure: alternatively, the copolymers may be obtained from Firestone as Stereon SR7879. Stereon SR7879 is a styrene-butadienyl-styrene block copolymer wherein the styrene (S) and butadienyl (B)

components may be arranged in any of the following configurations:

(S—B)n-S; (B—S)n (for n>1): or (B—S)n-B (for n>1). The copolymer has a tensile strength of 2,200 psi, a 300% modulus of 700 psi, an elongation of 750%, a melt flow index of 13 by ASTM Method Condition G and contains 41% bound styrene and 42 to 46% 1,2-butadienyl components, the remainder of the composition comprising the cis or trans moieties.

The tackifying resins useful in these adhesive compositions can be C5–C10 aliphatic or cycloaliphatic petroleum hydrocarbon resins, synthetic polyterpenes, hydrogenated rosin esters, and the like. More particularly, the useful tackifying resins include any compatible resins or mixtures thereof such as (1) C5–C10 aliphatic or cycloaliphatic petroleum hydrocarbon resins having a Ball and Ring softening point of from 70° to 150° C.; the latter resins resulting from the polymerization of olefins and diolefins; (2) glycerol and pentaerythritol esters of modified hydrogenated rosins, such, for example, as the glycerol ester of hydrogenated rosin, (3) copolymers and terpolymers of natural terpenes, e.g., styrene/terpene and alpha methyl styrene/terpene; (4) polyterpene resins having a softening point, as determined by ASTM method E28-58T, of from about 80° to 150° C.; the latter polyterpene resins generally resulting from the polymerization of terpene hydrocarbons, such as the bicyclic monoterpene known as pinene, in the presence of Friedel-Crafts catalysts at moderately low temperatures; also included are (5) the hydrogenated polyterpene resins; and (6) copolymers of aliphatic and aromatic monomers such as Wingtack 86 available from Goodyear Tire and Rubber Company. It has been found that the presence of the high vinyl levels in the block copolymer allows compatibility within the adhesive of a wider range of tackifying resins than are generally used in disposable applications. It has been particularly noted that the use of the more aliphatic tackifying resins such as the C5–C10 aliphatic petroleum hydrocarbon resins, resins which could not be used with the polymers utilized in U.S. Pat. No. 4,704,110, are especially suitable. The latter include Wingtack Extra, an aliphatic, aromatic hydrocarbon resin from Goodyear Chemicals; Escorez 5300 a partially hydrogenated cycloaliphatic petroleum hydrocarbon resin from Exxon Chemical Company; and Eastman Resin H 100 and/or H 130, partially hydrogenated cycloaliphatic petroleum hydrocarbon resins. The tackifier is present in these hot melt adhesive in an amount of 30 to 70%, preferably 50 to 60%, by weight.

Various plasticizing or extending oils are also present in the composition in amounts of 10% to about 30%, preferably 15 to 25%, by weight in order to provide wetting action and/or viscosity control. The usual plasticizing oils such as paraffinic and naphthenic oils are preferred; however, the invention also contemplates the use of the olefin oligomers and low molecular weight polymers as well as vegetable and animal oil and their derivatives. The petroleum derived oils which may be employed are relatively high boiling materials containing only a minor proportion of aromatic hydrocarbons (preferably less than 30% and, more particularly, less than 15% by weight of the oil). Alternatively, the oil may be totally non-aromatic. The oligomers may be polypropylenes, polybutenes, hydrogenated polyisoprene, hydrogenated polybutadiene, or the like having average molecular weights between about 350 and about 10,000. Vegetable and animal oils include glyceryl esters of the usual fatty acids and polymerization products thereof. Additionally, some or all of the oil or some portion of the tackifying resin may be replaced by a liquid tackifying resins such as Wingtack 10 (a low molecular weight liquid aliphatic synthetic polyterpene plasticizing resin).

Among the applicable stabilizers or antioxidants utilized herein are included high molecular weight hindered phenols and multifunctional phenols such as sulfur and phosphorous-containing phenols. Hindered phenols are well known to those skilled in the art and may be characterized as phenolic compounds which also contain sterically bulky radicals in close proximity to the phenolic hydroxyl group hereof. In particular, tertiary butyl groups generally substituted onto the benzene ring in at least one of the ortho positions relative to the phenolic hydroxy group. The presence of these sterically bulky substituted radicals in the vicinity of the hydroxyl group serves to retard its stretching frequency and, correspondingly, its reactivity; this stearic hindrance thus providing the phenolic compound with its stabilizing properties. Representative hindered phenols include: 1,3,5-trimethyl 2,4,6-tris (3,5-di-tert-butyl-4-hydroxybenzyl)benzene; pentaerythrityl tetrakis-3(3,5-di-tert-butyl-4-hydroxyphenyl)propionate; n-octadecyl-3(3,5-di-tert-butyl-4-hydroxyphenyl)-propionate; 4,4'methylenebis (2,6-tert-butylphenol); 4,4'-thiobis (6-tert-butyl-o-cresol); 2,6-ditertbutylphenol; 6-(4-hydroxphenoxy)-2,4-bis-(n-octylthio)-1,3,5-triazine; di-n-octadecyβ, 5-di-tert-butyl-4-hydroxy-benzylphosphonate; 2-(n-octylthio)ethyl 3,5-di-tert-butyl-4-hydroxy-benzoate; and sorbitol hexa[3-(3-di-tert-butyl-4-hydroxyphenyl)-propionate]; zinc di-n-butyl dithiocarbamate and zinc diethyl dithiocarbamate.

The performance of these antioxidants may be further enhanced by utilizing, in conjunction therewith known synergists such, for example, as thiodipropionate esters and phosphites, particularly useful is distearylthiodipropionate.

These stabilizers are generally present in amounts of about 0.1 to 2 weight percent, preferably 0.25 to 1.0%.

In formulating the hot melt adhesives of the present invention, the styrene-butadiene copolymer is used in an amount of 15 to 40% by weight, preferably 20 to 30%; with 30 to 70%, preferably 50 to 60%, of a tackifier; 10 to 30%, preferably 15 to 25%, of a plasticizing oil and a small effective amount of an antioxidant. Other additives such as waxes, pigments, dyestuffs conventionally added to hot melt adhesives for the various end uses contemplated may also be incorporated in minor amounts into the formulations of the present invention.

The adhesive compositions are prepared by blending the components in the melt at a temperature of about 130° to 200° C. until a homogeneous blend is obtained, approximately 2 hours. Various methods of blending are known to the art and any method that produces a homogeneous blend is satisfactory. An exemplary procedure involves placing the block copolymer, antioxidants and a portion of the oil in a jacketed mixing kettle, for example in a jacketed heavy duty mixer of the Baker-Perkins type, which is equipped with rotors and thereupon raising the temperature to a range of from about 120° to 180° C. When the mixture has been masticated to a uniform consistency, the tackifying resin and the remainder of the oil are gradually added in order to avoid the formation of lumps. Mixing and heating are continued until a smooth, homogeneous mass is obtained whereupon the remainder of the tackifying resin and the oil are thoroughly and uniformly admixed therewith. The resultant hot melt adhesives are generally produced in bulk form and packaged in release coated containers.

The adhesive is useful on any of the substrates generally employed in absorbent constructions including, but not limited to, tissue, nonwovens, polyethylene, polypropylene and other flexible polymeric films.

The resulting hot-melt pressure sensitive adhesive, once it is heated to a temperature where it will flow readily, can be applied directly to the outer covering layer of the absorbent structure or article it may be reverse (transfer) coated onto release paper using any of the techniques known in the art, including flow coating, roller coating, knife coating, or the like. The adhesive can also be extruded into place by using a hot-melt extruder or die face. In accordance with a preferred embodiment of the invention, the adhesive is applied to the absorbent structure using any of the above described techniques in such a manner that it acts as both a positioning and construction adhesive. Thus, an adhesive film could be coated onto silicone release liner and then transferred onto the outer layer of the absorbent using sufficient pressure to enable a portion of the adhesive to pass through the outer layer and form the required bond. Alternatively, the adhesive could be directly applied to the outer layer of the absorbent and pressure applied to again permit a portion thereof to permeate into the next substrate layer providing suitable bonding.

FIG. 1 depicts a top view of a representative absorbent product. 1 represents the garment facing surface of the absorbent product. The absorbent product may vary as to shape and size dependent upon its use. Such shapes and sizes are known in the art. 2 represents the hot melt adhesive composition which has been coated onto surface 1. The adhesive may be applied in any configuration, such configurations also being known in the art.

Figure 2:
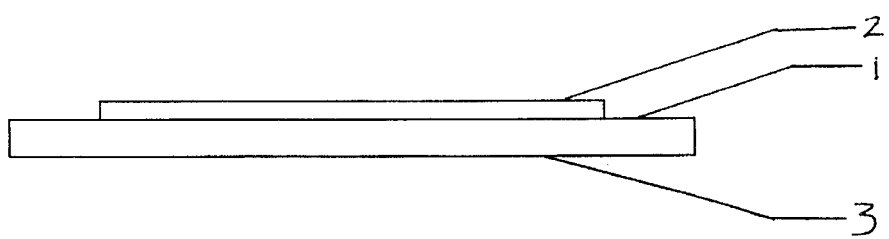
FIG. 2 depicts a side view of a representative absorbent product.

FIG. 2 depicts a side view of a representative absorbent product. 1 represents the garment facing surface of the absorbent product; 2 represents the hot melt adhesive composition which has been coated onto surface 1; and 3 represents the body facing surface of the absorbent product.

In the following illustrative examples, all parts are by weight and all temperatures in degrees Celsius unless otherwise specified. The hot melt adhesive compositions were prepared as described above and tested using the following procedures:

Samples were prepared for testing by coating a 1.75 to 2.25 mil thickness of the adhesive on a Mylar substrate (trademark of Dow Chemical Corp.). After conditioning overnight, 1 inch by 3 inch (2.54 by 7.82 cm) strips were cut in the X- machine direction. All tests were performed on samples as initially prepared and then repeated after subjecting the adhesives to heat aging at 175° C. for 24 hours.

40° C. Heat Resistance Test

The adhesive is coated onto paper, laminated to a second sheet of paper and allowed to equilibrate at room temperature for 24 hours. The coated samples are placed in a circulating air oven set at 40° C. One hundred gram weights are hung from the sample in a 180° peel mode and the time required to get bond failure is recorded in hours.

The longer the time to failure the higher the heat resistance of the product.

Needle Penetration Test (ASTM NORMD1321)

This test provides insight into softness or hardness of a hot melt adhesive by measuring the depth a needle of known weight penetrates into a sample.

Molten adhesive is poured into a mold and allowed to equilibrate at room temperature for 24 hours. The sample is put on the base of a penetrometer and the needle on the penetrometer is adjusted so it just contacts the surface of the adhesive.

The needle is released and allowed to penetrate into the adhesive for 5 seconds. A reading is taken from the penetrometer to determine how far the needle traveled.

A low value indicates a hard product and a high value indicates a soft product.

180° Cotton and Nylon Peel

The coated samples were laminated to cotton knit or nylon fabric by placing the fabric on glass plates in an oven equilibrated to 40° C. (or 50° as indicated). Test at 40° C.: the sample was placed on top of the fabric with a load of 70 grams per square inch for a period of 60 minutes. Test at 50° C.: the sample was placed on top of the fabric with a load of 135 grams per square inch for a period of 24 hours. In all cases, the sample was then peeled away from the fabric in a 180° direction using an Instron Tensile Tester at crosshead speed of 20 inches (500 mm) per minute. Values shown are for an average of at least three samples and are expressed in grams per linear inch. Any adhesive residue left on the cotton or nylon is noted qualitatively.

Cotton Peel Retention

The coated sample was laminated to cotton knit fabric by placing the knit on glass plates in an oven equilibrated to 40° C. and laminating with a 2 kg roller. Samples were tested initially and after 30 minutes. The sample was then peeled away from the cotton knit in 180° direction on an Instron Tester at crosshead speed of 20 inches (50 cm) per minute. Values shown are for an average of at least three samples and are expressed in grams per linear inch.

Tensile Strength

A molten mass of the adhesive was poured into a silicone rubber mold having central dimensions of 10 mm length and 12.5 mm width and end dimensions of 25×25 mm. A strip of silicone release paper is placed over the adhesive and compressed with a smooth lead weight. The sample is allowed to solidify and removed from the mold when completely cooled. Both ends of the molded adhesive specimen are covered with tape to prevent sticking to the jaws of the Instron. The thickness of the center of the sample is measured with a micrometer. The tensile strength of the specimen is then tested using an Instron tensile tester. The maximum load can be identified from a plot of load (force) vs elongation of the specimen, Stress at maximum load is measured as maximum load/area. Strain at maximum load is measured as the extension at maximum load/original length. This procedure also provides a measurement of % elongation which is the % stretch of the hot melt, e.g., 500% elongation is 5 times the original length.

Youngs modulus (modulus of elasticity) is obtained from the slope of the least squares fit straight line, made through the steepest linear region of the testing curve. High values indicate poor elasticity and low values indicate high elasticity.

TABLE I

|  | 1 | 2 | 3 | 4 |
|---|---|---|---|---|
| Stereon 840A | 22 | | | |
| Stereon SR7879 | | 22 | | |
| Kraton D1122 | | | 22 | |
| Cariflex TR 1102 | | | | 22 |
| ECR 179A | 54.5 | 54.5 | 54.5 | 54.5 |
| BP Enerpar M1930 | 23.5 | 23.5 | 23.5 | 23.5 |
| Antioxidant System | 0.3 | 0.3 | 0.3 | 0.3 |
| Viscosity: Sp21 20 rpm | | | | |
| 130° C. | 7915 | 6260 | 9350 | 9450 |
| 160° C. | 2380 | 1610 | 2750 | 3040 |
| Heat resistance 40° C. (hrs.) | 5 | 22 | 22 | 24 |
| Needle penetration (¹/₁₀ mm) | 104 | 95 | 68 | 93 |

Stereon 840A is a styrene butadiene block copolymer containing 43% styrene and about 8% 1,2-butadienyl moieties available from Firestone.
Kraton D1122 is a styrene butadiene block copolymer containing 40% styrene and about 8% 1,2-butadienyl moieties available from Shell Chemical.

TABLE I-continued

|   | 1 | 2 | 3 | 4 |
|---|---|---|---|---|

Cariflex TR1102 is a styrene butadiene block copolymer containing 29% styrene and about 5% 1,2-butadienyl from Shell Chemical.
ECR 179A is a C5/C9 aromatic/cycloaliphatic tackifying resin from Exxon.
BP Enerpar M1930 is a paraffin mineral oil with a pour point of −12° C. from BP Chemicals.

TABLE II

|   | 1 | 2 | 3 | 4 |
|---|---|---|---|---|
| COTTON: | | | | |
| Immediate | 198.2 | 119.4 | 117.0 | 182.0 |
| 30 mins RT % Retention | 199.9 | 109.6 | 81.33 | 157.6 |
| 1 hour 40° C. | 256.8 | 142.4 | 143.5 | 233.6 |
| 6 hours 40° C. | 438.3 | 227.5 | 275.0 | 475.0* |
| NYLON: | | | | |
| 1 hour 400° C. Blue Nylon | 485.7 | 234.6 | 303.5 | 377.9 |
| 24 hours 40° C. Blue nylon | 953.5 | 424.1 | 489.5 | 902.6 |
| 24 hours 50° C. Blue nylon | 1142* | 616 | 990.9** | 1174** |

*slight transfer
**heavy transfer

TABLE III

|   | 1 | 2 | 3 | 4 |
|---|---|---|---|---|
| Strain @ max load | 1296 | 1260 | 1579 | 1854 |
| Stress @ max load | 53.61 | 74.75 | 92.82 | 60.62 |
| Stress @ 500% elongation | 13.20 | 20.95 | 21.75 | 12.12 |
| Stress @ 1000% elongation | 45.18 | 67.32 | 61.75 | 33.00 |
| Youngs modulus | 7.42 | 10.84 | 8.602 | 5.045 |

The results presented above show that the adhesives containing the Stereon SR7879 block copolymer possessed a unique balance of properties including high cohesive strength coupled with lack of transfer even from the stringent nylon substrates. More specifically, Sample 2 shows the advantage of low viscosity at 160° C. and 130° C. which will enable the product to penetrate through nonwoven readily to allow the positioning adhesive assist in the construction of the napkin. This low viscosity also is more conducive to applications of adhesive directly to the pad vs. the conventional method of applying to release paper and transfer coating the adhesive to the napkin.

Further, Sample 2 also had a higher tensile strength (ultimate) shown on Table III under "Stress@Max Load" than Stereon 840A and 1102 based formulations, although not as high as the Kraton 1122 formulation. The latter formulation, however, was deficient with respect to its transfer properties. The combination of high tensile strength with low viscosity and low transfer is unique to the compositions described in the present invention.

Another series of samples was prepared using the various block copolymers but employing Eastotac H100R, an aliphatic hydrocarbon resin available from Eastman as the tackifying resin. The components and test results are shown in Tables IV, V and VI.

TABLE IV

|   | 5 | 6 | 7 | 8 |
|---|---|---|---|---|
| Stereon 840A | 22 | | | |
| Stereon 7879 | | 22 | | |
| Kraton G1122 | | | 22 | |
| Cariflex 1102S | | | | 22 |
| Eastotac H100R | 54.5 | 54.5 | 54.5 | 54.5 |
| BP Enerpar M1930 | 23.5 | 23.5 | 23.5 | 23.5 |
| Antioxidant | 0.3 | 0.3 | 0.3 | 0.3 |
| Viscosity: Sp21 20 rpm | | | | |
| 130° C. | 15100 | 19599 | 14900 | 13700 |
| 160° C. | 2600 | 2100 | 3100 | 3600 |
| Heat Resistance 40° C. (hrs.) | 6.78 | 9.26 | 1.64 | 2.17 |
| Needle penetration (1/10 mm) | 85 | 99 | 56 | 66 |

TABLE V

|   | 5 | 6 | 7 | 8 |
|---|---|---|---|---|
| Cotton: | | | | |
| Immediate | 105.9 | 203.0 | 56.96 | 73.27 |
| 30 mins RT % retention | 104.7 | 152.4 | 54.54 | 66.37 |
| 1 hour 40° C. | 221.0 | 211.2 | 102.9 | 168.7 |
| 6 hours 40° C. | 389.4 | 360.8 | 261.8 | 413.9 |
| Nylon: | | | | |
| 1 hour 40° C. blue nylon | 242.0 | 212.4 | 198.0 | 208.0 |
| 24 hours 50° C. blue nylon | 541.9 | 500.9 | 268.9 | 463.2 |
| 24 hours 50° C. blue nylon | 778.1* | 555.2 | 383.9 | 502.4* |

*slight transfer

The results presented in Tables IV and V show the better compatibility and greater pressure sensitivity of the adhesive composition containing the high vinylene content Stereon SR 7879 and the aliphatic resin as demonstrated by improved needle penetration (Table IV) and higher immediate cotton peel (Table V).

TABLE VI

|   | 5 | 6 | 7 | 8 |
|---|---|---|---|---|
| Strain @ max load | 44.34 | 62.96 | 77.39 | 61.22 |
| Stress @ max load | 1201 | 1112 | 1333 | 1572 |
| Stress @ 500% elongation | 15.58 | 19.91 | 25.19 | 16.98 |
| Stress @ 1000% elongation | 40.54 | 61.16 | 60.1 | 38.27 |
| Youngs modulus | 5.551 | 10.76 | 7.668 | 5.555 |

The results presented in Table V show a high immediate peel strength for Sample 6 accompanied by no transfer residue after 24 hours at 50° C. on nylon. Example 7 also passes the transfer test but has an immediate peel value that is unacceptable in positioning application.

The samples prepared above and identified as 2 and 6 find widespread use in positioning applications for disposable absorbent products, particularly for products wherein the adhesive is either transfer coated or directly coated onto the outer layer of the absorbent with sufficient pressure to permit some portion of the adhesive to permeate the outer layer and form a bond with the next substrate layer.

We claim:
1. An absorbent product comprising an elongated absorbent pad having a body facing surface and a garment facing surface, a portion of the garment facing surface being coated with the hot melt adhesive composition comprising:
   15 to 40% by weight of a styrene-butadiene-styrene block containing 30 to 50% styrene, the block copolymer having been polymerized so as to have a vinyl content greater than 35%
   30 to 70% by weight of a tackifying resin selected from the group consisting of C5–C10 aliphatic or cycloaliphatic petroleum hydrocarbon resins having a Ball and Ring softening point of 70° to 150° C.; modified hydrogenated rosins; glycerol and pentaerythritol esters of modified hydrogenated rosins; copolymers and terpolymers of natural terpenes; polyterpene resins having a softening point, as determined by ASTM method E28-58T, of from about 80 to 150° C.; aromatic petroleum hydrocarbon resins and the hydrogenated derivatives thereof; and copolymers of aliphatic and aromatic monomers;

10 to 30% by weight of naphthenic or paraffinic oil; and 0.1 to 2% by weight of an antioxidant; characterized in that the viscosity of the adhesive is 1000 to 3500 cps at 160° C. and the adhesive exhibits substantially no transfer.

2. The absorbent structure of claim 1 wherein the hot melt adhesive is applied to the pad in a manner such that it serves as both a positioning and construction adhesive.

3. The absorbent structure of claim 2 wherein the hot melt adhesive is applied directly to the garment facing surface.

4. The absorbent structure of claim 2 wherein the hot melt adhesive is transfer coated to the outer garment facing surface.

5. The absorbent structure of claim 1 wherein the block copolymer in the adhesive has a tensile strength of 2,200 psi, a 300% modulus of 700 psi, an elongation of 750%, a melt flow index of 13 at ASTM condition G and contains 41% bound styrene, 42 to 46% 1,2-butadienyl components, the remainder being a cis or trans butadienyl.

6. The absorbent structure of claim 1 wherein the styrene-butadiene-styrene block copolymer contains 40 to 50% styrene.

7. The absorbent structure of claim 1 wherein the tackifying resin in the adhesive is selected from the group consisting of C5–C10 aliphatic or cycloaliphatic petroleum hydrocarbon resins, synthetic polyterpenes and hydrogenated rosin.

8. The absorbent structure of claim 1 wherein the tackifying resin in the adhesive is selected from the group consisting of C5–C10 aliphatic or cycloaliphatic petroleum hydrocarbon resins having a Ball and Ring softening point of from 70 to 150° C., the latter resins resulting from the polymerization of olefins and diolefins; glycerol and pentaerythritol esters of modified hydrogenated rosins; copolymers and terpolymers of natural terpenes; polyterpene resins having a softening point, as determined by ASTM method E28-58T, of from about 80 to 150° C.; the hydrogenated polyterpene resins; and copolymers of aliphatic and aromatic monomers.

9. The absorbent structure of claim 1 wherein the hot melt adhesive comprises 20 to 30% by weight of the block copolymer, 50 to 60% by weight tackifying resin, and 15 to 25% by weight of the plasticizing oil.

10. The absorbent structure of claim 1 wherein the tackifying resin in the adhesive is a C5–C10 aliphatic or cycloaliphatic petroleum hydrocarbon resin.

11. An absorbent product comprising an elongated absorbent pad having a body facing surface and a garment facing surface, a portion of the garment facing surface being coated with the hot melt adhesive composition comprising:

15 to 40% by weight of a styrene-butadiene-styrene block containing 30 to 50% styrene, the block copolymer having been polymerized so as to have a vinyl content greater than 35%;

30 to 70% by weight of a C5–C10 aliphatic or cycloaliphatic petroleum hydrocarbon resins having a Ball and Ring softening point of 70° to 150° C.;

10 to 30% by weight of naphthenic or paraffinic oil; and 0.1 to 2% by weight of an antioxidant;

characterized in that the viscosity of the adhesive is 1000 to 3500 cps at 160° C. and the adhesive exhibits substantially no transfer.

12. The absorbent structure of claim 11 wherein the styrene-butadiene-styrene block copolymer contains 40 to 50% styrene.

* * * * *